(12) United States Patent
Murphy

(10) Patent No.: US 7,202,023 B2
(45) Date of Patent: Apr. 10, 2007

(54) HIGH THROUGHPUT SCREEN FOR INHIBITORS OF THE FOLATE BIOSYNTHETIC PATHWAY IN BACTERIA

(75) Inventor: Christopher K. Murphy, Upton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 847 days.

(21) Appl. No.: 09/925,824

(22) Filed: Aug. 9, 2001

(65) Prior Publication Data

US 2002/0164602 A1 Nov. 7, 2002

Related U.S. Application Data

(60) Provisional application No. 60/224,925, filed on Aug. 11, 2000.

(51) Int. Cl.
 *C12Q 1/68* (2006.01)
(52) U.S. Cl. ........................................... 435/6
(58) Field of Classification Search ................ 435/6, 435/7.1, 7.2; 556/24.1
 See application file for complete search history.

(56) References Cited

U.S. PATENT DOCUMENTS 6,153,381 A 11/2000 Rothstein ........................ 435/6

FOREIGN PATENT DOCUMENTS

EP 0 200 252 A1 12/1986
WO WO 01/48248 A2 7/2001

OTHER PUBLICATIONS

Rohlman et al., J. Bacter. 172, 12, pp. 7200-7210, 1990.*
Branch, TIBS 23, pp. 45-50, 1998.*
Bock et al., "A Simple and Rapid . . ." *Analytical Biochemistry* 86:238-251. 1978.
Bognar et al., "Folylpoly-γ-glutamate Synthetase-Dihydrofolate . . ." *The Journal of Biological Chemistry* 260(9):5625-5630, 1985.
Cronan et al., "Genetic and Biochemical . . ." *Journal of Bacteriology* 149(3):916-922. 1982.
De Saizieu et al., "Enzymic characterization of . . ." *Biochem. J.* 306(Pt2):371-337, 1995.
Hennig et al., "Crystal structure and . . ." *Nature Structural Biology* 5:357-362, 1998.
Herrington et al., "Measurement of the Uptake of Radioactive . . ." *Analytical Biochemistry* 216:427-430, 1994.
Huovinen "Increases in Rates . . ." *Clinical Infectious Diseases* 24(Suppl 1):S63-6, 1997.
Huovinen et al., "Trimethoprim and Sulfonamide . . ." *Antimicrobial Agents and Chemotherapy* 39(2)279-289, 1995.
Jones et al., "Cloning and Sequencing . . ." *Journal of Bacteriology* 175(7):2125-2130, 1993.
Merkel et al., "Characterization and sequence . . ." *FEMS Microbiology Letters* 143:247-252, 1996.

Myoda et al., "Cloning and mapping . . ." *Gene* 29:135-143, 1984.
Myoda et al., "Coregulation of dihydrofolate . . ." *Biochimica et Biophysical Acta* 842:99-103, 1985.
Nar et al., "Active site topology . . ." *Proc. Natl. Acad. Sci. USA* 92:121120-12125, 1995.
Slock et al., "An Apparent *Bacillus* . . ." *Journal of Bacteriology* 172(12):7211-7226, 1990.
Swedberg et al., "Characterization of mutationally . . ." *Journal of Bacteriology* 137(1):129-136, 1979.
Swedberg et al., "Sulfonamide Resistance in . . ." *Antimicrobial Agents and Chemotherapy* 42(5):1062-1067, 1998.
Viswanathan et al., "Kinetic Characterization of . . ." *Journal of Bacteriology* 177(20):5918-5923. 1995.
Xiao et al., "Crystal Structure of . . ." *Structure* 7:489-496. 1999.
Zimmerman et al., "Inhibitors of Folate . . ." *Journal of Medicinal Chemistry* 20(9):1213-15, 1977.
GenBank Accession No. L47709, Aug. 9, 2000.
Baigori et al., "Isolation and Characterization of *Bacillus subtilis* Mutants Blocked in the Synthesis of Pantothenic Acid," Journal of Bacteriology 173(13):4240-4242 (Jul. 1991).
Huang et al., "Protein Expression in Response to Folate Stress in *Escherichia coli*," Journal of Bacteriology 179(17):5648-5653 (Sep. 1997).
Kunst et al., "The complete genome sequence of the Gram-positive bacterium *Bacillus subtilis*," NATURE 390:249-256 + tables A-O (Nov. 20, 1997).
Kurtov et al., "The *Aspergillus nidulans panB* gene encodes ketopantoate hydroxymethyltransferase, required for biosyntehsis of pantothenate and Coenzyme A," Mol. Gen. Genet. 262:115-120 (1999).
Quinlivan et al., "Mechanism of the antimicrobial drug trimethoprim revisited," The FASEB Journal 14:2519-2524 (Dec. 2000).
Sahm et al., "D-Pantothenate Synthesis in *Corynebacterium glutamicum* and Use of *panBC* and Genes Encoding L-Valine Synthesis for D-Pantothenate Overproduction," Applied and Environmental Microbiology 65(5):1973-1979 (May 1999).
Wilson et al., "Exploring drug-induced alterations in gene expression in *Mycobacterium tuberculosis* by microarray hybridization," PNAS 96(22):12833-12838 (Oct. 26, 1999).
Sahm, et al., "D-Pantothenate Synthesis in *Corynebacterium glutamicum* and Use of *panBC* and Genes Encoding L-Valine Synthesis for D-Pantothenate Overproduction," *Applied and Environmental Microbilogy*, 65(5):1973-1979 (1999).

* cited by examiner

*Primary Examiner*—Nancy Vogel
(74) *Attorney, Agent, or Firm*—Fish & Richardson P.C.

(57) ABSTRACT

Methods for identifying compounds that are inhibitors of bacterial tetrahydrofolate biosynthesis are disclosed. Such compounds can be used as lead compounds in methods for preparing antibacterial agents for treating bacterial infections (e.g., in humans, animals, and plants). The disclosed methods allow for high throughput screening of libraries of test compounds.

23 Claims, 4 Drawing Sheets

SEQUENCE LISTING

```
<160> NUMBER OF SEQ ID NOS: 3

<210> SEQ ID NO 1
<211> LENGTH: 494
<212> TYPE: DNA
<213> ORGANISM: Bacillus subtilis

<400> SEQUENCE: 1
gctaatgtgt tggtacaagc ccgttgattt tggtatactt ccattgggca gtatcgcctg      60
cgaactgcac ctattattaa aatagataga cattgcagca gtctgccttg atccaaaaaa     120
ggactgggac agagggatga aactcgccga actttagaaa gtgaagaatc cttctcgttg     180
taacggaagg ttttttggct tgcagaagaa aacggcagat catctcctct aaacatgagg     240
aggagaaaac atgaaaacaa aactggattt tctaaaaatg aaggagtctg aagaaccgat     300
tgtcatgctg accgcttatg attatccggc agctaaactt gctgaacaag cgggagttga     360
catgatttta gtcggtgatt cacttggaat ggtcgtcctc ggccttgatt caactgtcgg     420
tgtgacagtt gcggacatga tccatcatac aaaagccgtt aaaagggtg cgccgaatac      480 ctttattgtg acag                                                       494

<210> SEQ ID NO 2
<211> LENGTH: 32
<212> TYPE: DNA
<213> ORGANISM: Artificial Sequence
<220> FEATURE:
<223> OTHER INFORMATION: primer for PCR

<400> SEQUENCE: 2
ccggaattcg ctaatgtgtt ggtacaagcc cg                                    32

<210> SEQ ID NO 3
<211> LENGTH: 32
<212> TYPE: DNA
<213> ORGANISM: Artificial Sequence
<220> FEATURE:
```

-continued

```
<223> OTHER INFORMATION: primer for PCR

<400> SEQUENCE: 3
cgcggatccc aataaaggta ttcggcgcac cc                              32
```

HIGH THROUGHPUT SCREEN FOR INHIBITORS OF THE FOLATE BIOSYNTHETIC PATHWAY IN BACTERIA

CROSS-REFERENCE TO RELATED APPLICATION

This application claims priority from U.S. provisional application Ser. No. 60/224,925 filed on Aug. 11, 2000, which is incorporated herein by reference in its entirety.

FIELD OF THE INVENTION

The invention relates to methods for identifying inhibitors of tetrahydrofolate biosynthesis in bacteria.

BACKGROUND OF THE INVENTION

Tetrahydrofolate is an essential cofactor for many biosynthetic enzymes. It acts as a carrier of one-carbon units in the syntheses of such critical metabolites as methionine, purines, glycine, pantothenate, and thymidylate. For example, the enzyme ketopantoate hydroxymethyl transferase, encoded by the panB gene, requires a tetrahydrofolate cofactor to synthesize precursors of pantothenate. As tetrahydrofolate is synthesized de novo in bacteria, inhibition of its synthesis kills cells. Indeed, two very effective antibiotics, sulfonamide and trimethoprim, kill bacterial cells by blocking tetrahydrofolate production. These two antibiotics, which are often used in combination with each other, are commonly prescribed for the treatment of urinary tract infections, enteric infections such as shigellosis, and respiratory tract infections. The success of these drugs is indicative of the vulnerability of many pathogenic bacteria to inhibitors of tetrahydrofolate synthesis.

Bacteria have a multiple step pathway for the synthesis of the tetrahydrofolate cofactor. In one branch of the pathway, the metabolites chorismate and glutamine are substrates for aminodeoxychorismate synthase, encoded by the *B. subtilis* genes, pabA and pabB, which produces 4-amino 4-deoxychorismate. Aminodeoxychoismate lyase, encoded by *B. subtilis* pabC, then converts 4-amino 4-deoxychorismate to para-aminobenzoic acid (PABA), an important precursor. In another branch, a number of enzymes, including those encoded by *B. subtilis* mtrA, folA, and folK, produce the precursor 2-amino-4-hydroxy-6-hydroxy methyl-7,8-dihydroxpteridine diphosphate. This precursor and PABA are substrates for dihydropteroate synthetase, encoded by the *B. subtilis* sul gene (homologous to the *E. coli* dhps and folP genes), which produces dihydropteroate. Sulfonamides, such as sulfamethoxazole, are competitive inhibitors of dihydropteroate synthase.

Dihydropteroate is modified by the bifunctional enzyme encoded by *B. subtilis* folC to produce dihydrofolate. Finally, DHFR (dihydrofolate reductase), encoded by *B. subtilis* dfrA, modifies this dihydrofolate to generate the end product tetrahydrofolate. Trimethoprim is a competitive inhibitor of bacterial DHFRs. This selectivity is critical, as eukaryotic DHFRs are unimpeded by the antibiotic.

The emergence of antibiotic resistant strains of bacteria has heightened the urgency of developing new antibiotics. Indeed, resistance to sulfonamides and trimethoprim is prevalent and spreading. For example, before 1983, trimethoprim resistance in *Shigella* was rare and occurred in less than 4% of cases. However, by the 1990s, the frequency of resistance in isolates was as much as 52% (Huovinen (1997) *Clinical Infectious Disease* 24 (Suppl. 1):S63–66). Similarly, as many as 42% of *Shigella* species are sulfonamide resistant (Huovinen, supra). Often resistance to these antibiotics is a plasmid borne trait that can be transmitted horizontally to other bacterial species.

SUMMARY OF THE INVENTION

The invention is based upon the discovery that the activity of promoters of certain genes is increased in the presence of compounds that inhibit *B. subtilis* tetrahydrofolate biosynthesis. Thus, compounds that inhibit tetrahydrofolate biosynthesis can be identified by their ability to increase the activity of the *B. subtilis* panB promoter. Various promoters can be used in the invention, provided that the activity of the promoter is upregulated by a tetrahydrofolate biosynthesis inhibitor, such as trimethoprim or sulfonamide. Tetrahydrofolate biosynthesis inhibitors that slow the growth of, or kill, bacteria are candidate antibacterial agents that can be used in methods of treating bacterial infections. The invention thus provides a rapid and convenient method for identifying (i) compounds that inhibit tetrahydrofolate biosynthesis and which can subsequently be derivatized to produce antibacterial agents, as well as (ii) compounds that inhibit tetrahydrofolate biosynthesis and which are antibacterial agents. If desired, such inhibitors of tetrahydrofolate synthesis can be further derivatized using standard medicinal chemistry techniques to produce anti-microbials of increased potency.

Accordingly, the invention features a method for determining whether a test compound is an inhibitor of bacterial tetrahydrofolate biosynthesis. The method includes: (i) contacting a bacterial cell with a test compound, wherein the bacterial cell contains (a) a promoter (e.g., panB), the activity of which is increased in the presence of a compound that inhibits tetrahydrofolate biosynthesis, operably linked to (b) a reporter gene; and (ii) measuring activity of the promoter, wherein an increase in activity, relative to the level of activity of the promoter in the absence of the test compound, indicates that the test compound is an inhibitor of bacterial tetrahydrofolate biosynthesis.

The invention also includes a method for determining whether a test compound is an antibacterial agent, the method comprising: (i) contacting a bacterial cell with a test compound, wherein the bacterial cell contains (a) a promoter (e.g., panB), the activity of which is increased in the presence of a compound that inhibits tetrahydrofolate biosynthesis, operably linked to (b) a reporter gene; (ii) measuring activity of the promoter, wherein an increase in activity, relative to the level of activity of the promoter in the absence of the test compound, indicates that the test compound is an inhibitor of tetrahydrofolate biosynthesis; and (iii) determining whether the compound is an antibacterial agent by determining whether the compound kills, or slows the growth of, bacteria. Optionally, the test compound may be further assayed in a biochemical assay (e.g., in an extract of the cell) to determine which step in the pathway is inhibited, and to confirm that the test compound inhibits tetrahydrofolate biosynthesis. For example, inhibition of tetrahydrofolate biosynthesis can be detected as inhibition of incorporation of para-aminobenzoic acid (PABA) into cells. Conventional methods can be used to measure inhibition of incorporation of PABA into cells (Herrington (1994) *Anal Biochem* 216:427–430). Other optional tests can be incorporated into the method. For example, growth inhibition and antibacterial effect of the test compound can assayed. The assay can be a plate assay or a liquid culture assay in a microplate. The assay can be performed with *B. subtilis* cells, but also with any Gram-positive or Gram-negative bacterial strain that grows in culture.

An increase in activity of the promoter can be measured, for example, by measuring expression of a reporter gene that is operably linked to the promoter, such as a lacZ, cat, gus, a green fluorescent protein gene, or a luciferase gene. Other suitable reporter genes are well known in the art and can be used in the invention. If desired, the activity of the promoter can be measured by measuring binding of antibodies to a product of the reporter gene (e.g., a protein encoded by the reporter gene), with an increase in the level of bound antibodies reflecting an increase in activity of the promoter. Alternatively, activity can be measured by measuring the level of mRNA transcribed from the reporter gene, with an increase in the mRNA level reflecting an increase in promoter activity. Further, the expression of the panB, panC, and panD genes can be measured by determining the levels of the panB, panC, and panD polypeptides, for example, using antibodies specific to the polypeptides. Alternatively, enzymatic assays can be performed on crude cell extracts for aspartate 1-decarboxylase activity (panD), pantothenate synthase activity (panC), and ketopantoate hydroxymethyltransferase activity (panB) (see Cronan et al. (1982) *J Bact*149:916–922).

The invention also provides methods of preparing (i) an inhibitor of tetrahydrofolate biosynthesis and/or (ii) an antibacterial agent. The methods include: screening multiple test compounds by the methods described above; identifying candidate compounds that upregulate promoter activity; isolating one or more lead compounds from the candidate compounds; identifying and selecting a lead compound that inhibits tetrahydrofolate biosynthesis or bacterial growth; and formulating the selected lead compound as an inhibitor of tetrahydrofolate biosynthesis or as an antibacterial agent. A "lead compound" is a test compound that increases promoter activity to a level at least three times the standard deviation above the mean of a group of non-active compounds or controls. If desired, lead compounds can be subsequently derivatized using conventional medicinal chemistry methods, as described herein.

Similarly, the invention features methods for preparing (i) an inhibitor of tetrahydrofolate biosynthesis or (ii) an antibacterial agent. The methods include screening multiple test compounds by the methods described above; identifying candidate compounds that upregulate promoter activity; isolating one or more lead compounds from the candidate compounds; derivatizing the lead compound(s), thereby producing a derivative of the lead compound; identifying derivatives that inhibit tetrahydrofolate biosynthesis or bacterial growth; and formulating the derivative as an inhibitor of tetrahydrofolate biosynthesis or as an antibacterial agent (e.g., by admixture with a pharmaceutically acceptable carrier). Inhibitors of tetrahydrofolate biosynthesis and antibacterial agents prepared by such methods also are included within the invention. Such compounds can be used in methods for inhibiting bacterial tetrahydrofolate biosynthesis or growth of bacteria in an organism having a bacterial infection.

As used herein, the term "operably linked" requires that a nucleic acid sequence is connected to a promoter sequence in a manner, which allows for transcriptional expression of the nucleotide sequence in vivo.

The invention offers several advantages. For example, various embodiments of the invention can readily be used for high-throughput screening (HTS) of a wide variety of test compounds. Thus, lead compounds can readily be selected from a large number of test compounds. Assays employing the panB promoter are capable of detecting tetrahydrofolate biosynthesis inhibitors at concentrations both above and below their minimal inhibitory concentration (MIC). Thus, the assays described herein provide a high level of sensitivity and are expected to detect growth inhibitory (i.e., bacteriocidal) compounds, as well as less potent inhibitors of the tetrahydrofolate biosynthesis pathway, which can be subsequently modified using standard medicinal chemistry techniques and by evaluating structure-activity relationship (SAR) data. Because the assays are cell-based, they can be used to identify antibacterial agents that can efficiently enter bacterial cells. Thus, the assays enable the identification of potent antibacterial compounds and compounds of structural interest that may have relatively modest potency, but have favorable cell permeability properties. In addition, because tetrahydrofolate is the product of a multi-step biochemical pathway, the methods disclosed herein enable the identification of compounds that may inhibit any enzymatic function or step in the pathway.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, technical manuals, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following description of the preferred embodiments thereof, and from the claims.

DETAILED DESCRIPTION

Figure 1:
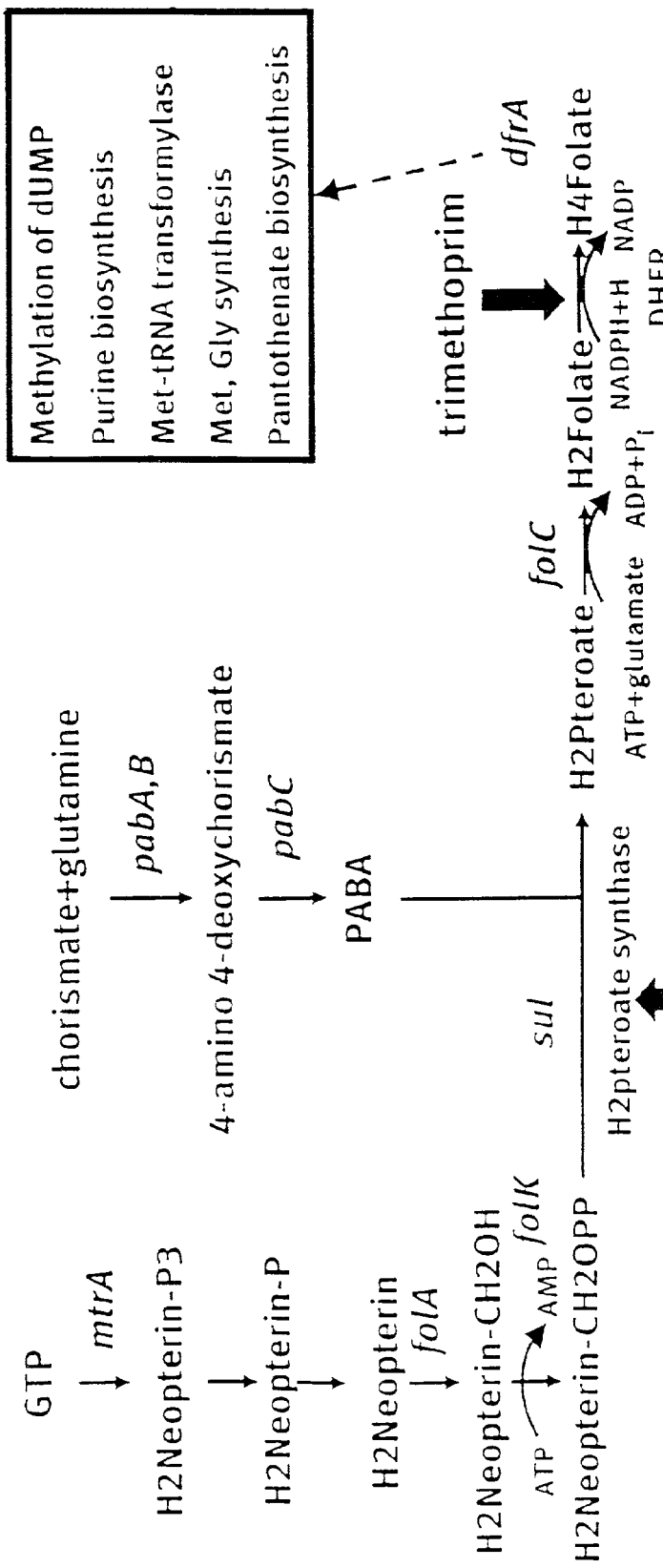
FIG. 1 is a schematic representation of the bacterial tetrahydrofolate biosynthesis pathway. The targets of the tetrahydrofolate biosynthesis inhibitors, sulfamethoxazole and trimethoprim, are shown.

The invention provides methods for determining whether a test compound is an inhibitor of bacterial tetrahydrofolate biosynthesis. The invention derives from the discovery that compounds that inhibit tetrahydrofolate biosynthesis cause an increase in the expression of the panBCD operon. As discussed in detail below, the activity of the panB promoter is increased upon inhibition of the tetrahydrofolate biosynthesis pathway. Generally, the methods of the invention involve determining whether the test compound induces an increase in activity in the panB promoter, as indicated by an increase in expression of a reporter gene operably linked to the promoter (i.e., a reporter-based screen). Thus, compounds that increase the activity of the panB promoter can be expected to inhibit bacterial tetrahydrofolate biosynthesis. Optionally, the test compound can be further tested to confirm that it inhibits tetrahydrofolate biosynthesis (i.e., in a biochemical screen). These methods are described in further detail below.

Part I: Reporter-Based Screens

Genetic Constructs: Conventional transcriptional profiling methods can be used to identify promoters that have increased activity in the presence of antibacterial agents such as trimethoprim and sulfamethoxazole, which are inhibitors of tetrahydrofolate biosynthesis. In such an assay, certain bacterial promoters display an increase in activity in the presence of antibacterial agents, as evidenced by an increase in the level of mRNA transcripts of the sequences.

A "promoter" is a minimal sequence sufficient to direct transcription; the promoter is located in the 5' region of a native gene. A sequence containing the panB promoter is set forth as SEQ ID NO:1. GenBank entry Accession No. L47709 contains a listing of the sequence of the B. subtilis panB operon as well as flanking sequences. The panB promoter can be found in the region of about nucleotide 13043 to about 13536 in the GenBank entry L47709.

To confirm that the activity of a promoter is increased in the presence of an antibacterial agent, each promoter can be operably linked to the coding sequence of a reporter gene, such as the E. coli lacZ gene. The resulting genetic constructs then are inserted into a plasmid, which is stably propagated, e.g., in B. subtilis. Such strains are treated with an antibacterial agent, such as trimethoprim and sulfamethoxazole, and the level of promoter activity, as measured by lacZ expression is measured. An increase in the level of promoter activity, relative to the level of lacZ expression in untreated, control cells, confirms that promoter activity is modulated by the antibacterial agent.

The "reporter gene" can be any sequence the expression of which can be detected or measured, other than the coding sequence to which the promoter naturally is operably linked. Typically, the reporter gene is heterologous to the bacterial strain in which promoter activity is measured. Examples of suitable reporter genes include, without limitation, lacZ, the bacterial chloramphenicol acetyltransferase (cat) gene, luciferase genes, the bacterial gus gene, and the like. Also included are sequences that encode fluorescent markers, such as green fluorescent protein (GFP). The aforementioned reporter genes, and methods for measuring their expression, are well known in the art.

Bacterial Strains: B. subtilis strains having the panB promoter operably linked to the coding sequence of a reporter gene can be used to assay the ability of test compounds to increase activity of the panB promoter. If desired, the promoter and reporter gene can be stably integrated into the bacterial chromosome. Alternatively, the panB promoter and coding sequence of the reporter gene can be located on a plasmid that is introduced into a bacterium (e.g., E. coli).

Test Compounds: The "test compound" can be any compound, such as a small organic or inorganic molecule, amino acid, polypeptide, nucleic acid, peptide nucleic acid, carbohydrate, or polysaccharide. The test compounds can be synthetic, naturally occurring, or a combination of synthetic and natural components. If desired, the test compound can be a member of a library of test compounds (e.g., a combinatorial chemical library) or a component of a cellular extract or bodily fluid (e.g., urine, blood, tears, sweat, or saliva).

Test compounds that increase the activity of the promoter, relative to the level of promoter activity in the absence of the test compound, are considered inhibitors of bacterial tetrahydrofolate biosynthesis. The level of promoter activity measured in the presence of the test compound then is compared with the level measured in the absence of the test compound. Generally, an increase in the level of promoter activity that is at least 3 times the standard deviation of a test compound set (i.e., a set of one or more test compounds), plus the mean of a test compound set, relative to the level of gene expression in the absence of the test compound, indicates that the test compound is an inhibitor of tetrahydrofolate biosynthesis. Such an increase may be, for example, 5-fold, 10-fold, 20-fold, 50-fold, or even 100-fold. A relatively high level of induction generally indicates that the test compound has a relatively high level of potency.

Promoter activity, as measured by reporter gene expression, can be measured by any of a number of conventional methods, and the optimal method will depend upon factors such as the nature and function of the reporter gene. In general, suitable assays of reporter gene expression include methods such as (i) assaying the function of a product of the reporter gene (e.g., measuring an enzymatic reaction catalyzed by a product of the reporter gene); (ii) measuring the level of protein expressed from the reporter gene (e.g., by SDS-PAGE or in an immunoassay using antibodies (e.g., polyclonal or monoclonal antibodies) that specifically bind to the product of the reporter gene; and (iii) measuring the level of mRNA transcribed from the reporter gene. Included within the invention are assays that permit high throughput screening of test compounds.

The assays of promoter induction can be carried out in virtually any reaction vessel or receptacle. Examples of suitable receptacles include 96-well plates, 384-well plates, test tubes, centrifuge tubes, and microcentrifuge tubes. The methods can also be carried out on surfaces such as metal, glass, ceramics, paper, polymeric chips, membrane surfaces, resins, or the surface of a matrix-assisted laser-desorption ionization mass spectrometry (MALDI-MS) plate.

Part II: Biochemical Screen

Once a test compound is identified as an inhibitor of tetrahydrofolate biosynthesis using the above-described reporter-based assay, the compound is thus a potential or candidate anti-bacterial agent. Candidate compounds can be further tested with a simple cell-based assay, or if desired, in a biochemical assay. One simple cell-based assay is the uptake by cells of radio-labeled PABA from the media. Herrington (1994) Anal Biochem 216:427–430 described such an assay using $^{14}$C-PABA and demonstrated that PABA uptake is inhibited by treatment with trimethoprim and sulfathiazole. The details of this assay are set forth below.

Candidate compounds identified in the above-described screen can be tested in an in vitro biochemical assay for their ability to inhibit an enzymatic step in the synthesis of tetrahydrofolate. Candidate compounds, which are effective inhibitors in a biochemical assay, can be considered "lead" compounds or may be antibacterial agents.

For example, candidate compounds can be tested for their ability to inhibit enzymes encoded by tetrahydrofolate biosynthesis genes, such as B. subtilis mtrA, folA, folK, sul, pabA, pabB, pabC, folC, and dfrA. Various methods for measuring inhibition of steps in tetrahydrofolate biosynthesis are known in the art, and can be used in this aspect of the invention (see, e.g., Nar et al. (1995) *Proc Natl Acad Sci USA* 92:12120–25; Zimmerman et al. (1977) *J Med Chem* 20:1213–15; Bock et al. *Anal Biochem* (1978) 86:238–51; Swedberg et al. (1979) *J Bact* 137:129–136; Viswanathan et al. (1995) *J Bact* 177:5918–5923; Bognar et al. (1985) *J Biol Chem* 1985; 260:5625–30; Myoda et al. (1984) Gene 29:139–147). Table 1 sets forth various *B. subtilis* and *E. coli* tetrahydrofolate biosynthesis genes and enzymes, along with the enzymatic reactions that the enzymes catalyze. Standard assays for measuring inhibition of the enzymatic reactions are summarized in Table 1 and can be used in the invention.

e.g., as a dry or liquid additive, or it can be generated in situ (e.g., as the product of another reaction). The substrate can be detectably labeled with a tag, for example, a radiolabel, a fluorescent label, a magnetic label, or as a biotinylated derivative.

After incubation of the cell extract/substrate mixture under conditions that normally allow the particular step(s) to proceed, the mixture is assayed to determine whether the substrate remains and/or whether the corresponding product or products have been formed. The optimal duration of incubation varies with the particular synthesis step(s) being

TABLE 1

Assays of Tetrahydrofolate Biosynthesis Enzymes

| Enzyme Activity | Gene Name | Reaction Catalyzed by the Enzyme | Assay | Reference |
|---|---|---|---|---|
| GTP cyclohydrase I | mtrA | GTP ↔ 7,8 dihydroneopterin triphosphate | measure neopterin fluorometrically (excite 365 nm, emission 446 nm) after reverse-phase HPLC | Nar et al. (1995) Proc Natl Acad Sci USA 92:12120–25. |
| 7,8 dihydroneopterin aldolase (DHNA) | folA | 7,8 dihydroneopterin ↔ 6-hydroxymethyl-7,8-dihydropterin + glycoaldehyde | Production of [$^{14}$C]glycoaldehyde from dihydroneopterin | Zimmerman et al. (1977) J Med Chem 20:1213–15 |
| 6-Hydroxymethyl-7,8-dihydropterin pyrophosphokinase (HPPK) | folK | ATP + 6-hydroxymethyl-7,8-dihydropterin ↔ AMP + 6-hydroxymethyl-7,8-dihydropterin pyrophosphate | Thin-layer chromatography of reaction products | Bock et al. Anal Biochem (1978) 86:238–51 |
| Dihydropteroate Synthase (DHPS) | sul/folP/dhps | PABA ↔ dihydroxypteroate | Incorporation of [$^{14}$C]PABA into dihydropteroic acid | Swedberg et al. (1979) J Bact137:129–136. |
| aminodeoxychorismate synthase | pabAB | chorisimate + glutamine ↔ 4-amino 4-deoxychorismate ↔ | Assay PABA production fluorimetrically from glutamine & chorismate | Viswanathan et al (1995) J Bact 177:5918–5923 |
| aminodeoxychorismate lyase | pabC | 4-amino 4-deoxychorismate ↔ PABA | Assay PABA production fluorimetrically | Viswanathan et al. (1995) J Bact 177:5918–5923 |
| Dihydrofolate: folylpolyglutamate synthetase | folC | dihydropteroate + ATP + glutamate ↔ dihydrofolate + ADP + Pi | Incorporation of [$^{14}$C] glutamate into folate products. | Bognar et al. (1985) J Biol Chem 1985; 260:5625–30 |
| Dihydrofolate reductase | dfrA | dihydrofolate + NADPH + H + ↔ tetrahydrofolate + NADP | Assay reduction of dihydrofolate spectrophotometrically at 340 nm. | Myoda et al. (1984) Gene 29:139–147. |

If desired, inhibition of tetrahydrofolate biosynthesis can be measured in a cell extract that contains all of the components (e.g., enzymes, cofactors, carrier molecules, and buffers) normally necessary for a particular step that is needed in the synthesis of folates. Cell extracts containing enzymes, cofactors, and carrier molecules can be cytoplasmic, cytosolic, or membrane preparations, whole cells, or naturally occurring or synthetic mixtures composed of natural or unnatural components, or both. Carrier molecules included in the cell extract can include numerous components, such as molecular transport machinery and membranes. The substrate for the reaction can be contained within the cell extract initially, it can be added in solution, carried out and also with incubation temperature (e.g., at least 30 minutes, 1 hour, 2 hours, 3 hours, 5 hours, 8 hours, 12 hours, or longer, at, e.g., room temperature or lower, 30° C., 37° C., or higher, depending on the strain of bacteria).

Medicinal Chemistry

Once a compound has been identified as a lead compound for inhibiting tetrahydrofolate biosynthesis, principles of standard medicinal chemistry can be used to produce derivatives of the compound. Derivatives can be screened for improved pharmacological properties, for example, efficacy, pharmacokinetics, mammalian toxicity, stability, solubility, and clearance. The moieties that are responsible for the compound's activity can be revealed by examining its structure-activity relationships (SAR). Specifically, a person of ordinary skill in the art of chemistry could modify a moiety of the compound to study the effects of the modification on the potency of the compound and thereby produce derivatives of the compound having increased potency (See, e.g., Nagarajan et al., Antibiot. 41:430–438). For example, chemical modifications such as N-acylation, esterification, hydroxylation, alkylation, amination, amidation, oxidation, or reduction can be made. Such chemical modifications can be made according to conventional methods (See, e.g., Wade, Organic Chemistry, Prentice-Hall, Inc., New Jersey, 1987). In addition, structural information can be used to design and optimize derivatives of the inhibitor by using molecular modeling software and conventional methods. Molecular modeling software is commercially available (e.g., from Tripos Inc., Molecular Simulations, Inc., and MDL Information Systems, Inc).

Use of Tetrahydrofolate Biosynthesis Inhibitors

A compound identified as a tetrahydrofolate biosynthesis inhibitor and/or as an antibacterial agent can be used to treat a bacterial infection in an organism (e.g., a plant or a mammal (e.g., a human, dog, cat, or cow)). Because tetrahydrofolate biosynthesis genes are widely conserved, inhibitors of tetrahydrofolate biosynthesis are expected to be useful in inhibiting tetrahydrofolate biosynthesis in a wide spectrum of bacteria. For example, the compounds can be used to treat infections of gram-positive bacteria, particularly pathogenic bacteria, such as *Streptococcus* species, *Staphylococcus* species, and *Clostridia* species. Thus, the compounds can be used, for example, to treat infections caused by *Streptococcus pneumoniae, Streptococcus pyogenes, Streptococcus agalactiae, Streptococcus endocarditis, Streptococcus faecium, Streptococcus sangus, Streptococcus viridans,* or *Streptococcus hemolyticus*. In other applications, the compounds can be used to treat infections of gram negative bacteria, e.g., *Shigella, E. coli, Klebsiella, Yersinia,* and *H. influenzae*.

A composition containing an effective amount of a tetrahydrofolate biosynthesis inhibitor or an antibacterial agent can be administered (e.g., topically, orally, nasally, buccally, subcutaneously, or intraperitoneally) to an organism in a method of treatment. Treatment typically includes administering an effective amount of a composition containing a tetrahydrofolate biosynthesis inhibitor or an antibacterial agent to a subject in need of such treatment, thereby inhibiting bacterial growth in the subject. Such a composition typically contains from about 0.1 to 90% by weight (e.g., 1 to 20% or 1 to 10%) of the antibacterial agent of the invention in a pharmaceutically acceptable carrier.

Solid formulations of the compositions for oral administration may contain suitable carriers or excipients such gelatin, lactose, acacia, sucrose, kaolin, mannitol, dicalcium phosphate, calcium carbonate, sodium chloride, or alginic acid. Disintegrators that can be used include, without limitation, micro-crystalline cellulose, corn starch, sodium starch glycolate and alginic acid. Tablet binders that may be used include acacia, methylcellulose, sodium carboxymethylcellulose, polyvinylpyrrolidone (Povidone™), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a composition containing the compound and a physiologically acceptable excipient is infused. Physiologically acceptable excipients may include, for example, 5% dextrose, 0.9% saline, Ringer's solution or other suitable excipients. For intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid (e.g., ethyl oleate).

A topical semi-solid ointment formulation typically contains a concentration of the active ingredient from about 0.1 to 20% wt/vol (e.g., 0.1 to 2% wt/vol of essentially pure material) in a carrier such as a pharmaceutical cream base. Various formulations for topical use include drops, tinctures, lotions, creams, solutions, and ointments containing the active ingredient and various supports and vehicles.

The optimal percentage of the active ingredient in each composition varies according to the formulation itself and the therapeutic effect desired. Appropriate dosages can be readily determined by those of ordinary skill in the art by monitoring an organism for signs of disease amelioration or inhibition, and increasing or decreasing the dosage and/or frequency of treatment as desired. The optimal amount of the composition used for treatment of conditions caused by or contributed to by bacterial infection may depend upon the manner of administration, the age and the body weight of the subject and the condition of the subject to be treated. Generally, the antibacterial agent is administered to a subject at a dosage of 1 to 100 mg/kg of body weight (e.g., at a dosage of 1 to 10 mg/kg of body weight).

EXAMPLES

The invention is further described by the following examples, which are not intended to limit the scope of the invention.

Example 1

Identification of the panB Promoter

Conventional RNA profiling studies revealed that bacterial cells treated with the tetrahydrofolate biosynthesis pathway inhibitors trimethoprim (0.2 µg/ml or 10 µg/ml) and sulfamethoxazole (0.5 mg/ml or 2 mg/ml) in LB medium at 37° C. for about 40, 60, 80, or about 100 minutes displayed an increase in levels of mRNA derived from the panB, panC, and panD genes. After 90 minutes of treatment with 10 µg/ml trimethoprim, panB mRNA levels were induced 10 fold, panC 54 fold, and panD 38 fold. Similarly, after 80 minutes of treatment with 0.5 mg/ml sulfamethoxazole, panD mRNA levels were induced 148 fold. panB, panC, and panD are located in close proximity to each other, and all are oriented in the same direction as described in Merkel and Nichols, (1996) *FEMS Microbiology Letters* 143:247–252). panB, panC, andpanD are expected to be transcribed in a single mRNA from the panBCD operon and hence to share the panB promoter. Transcriptional profiling indicated that the panB promoter is upregulated by antibacterial agents trimethoprim and sulfamethoxazole.

B. subtilis strains containing a panB promoter (along with an insignificant portion of the coding sequence) operably linked to the coding sequence of an *E. coli* lacZ reporter gene were used to confirm that the activity of the promoter is upregulated by an inhibitor of tetrahydrofolate biosynthesis. The sequence of the panB promoter

```
(SEQ ID NO:1:
"5'GCTAAATGT GTTGGTACAA GCCCGTTGAT TTTGGTATAC

TTCCATTGGG CAGTATCGCC TGCGAACTGC ACCTATTATT

AAAATAGATA GACATTGCAG CAGTCTGCCT TGATCCAAAA

AAGGACTGGG ACAGAGGGAT GAAACTCGCC GAACTTTAGA

AAGTGAAGAA TCCTTCTCGT TGTAACGGAA GGTTTTTTGG

CTTGCAGAAG AAAACGGCAG ATCATCTCCT CTAAACATGA

GGAGGAGAAA ACATGAAAAC AAAACTGGAT TTTCTAAAAA

TGAAGGAGTC TGAAGAACCG ATTGTCATGC TGACCGCTTA

TGATTATCCG GCAGCTAAAC TTGCTGAACA AGCGGGAGTT

GACATGATTT TAGTCGGTGA TTCACTTGGA ATGGTCGTCC

TCGGCCTTGA TTCAACTGTC GGTGTGACAG TTGCGGACAT

GATCCATCAT ACAAAAGCCG TTAAAAGGGG TGCGCCGAAT

ACCTTTATTG TGACAG")
``` is described in GenBank Accession Number L47709. The promoter was isolated by PCR amplification of *B. subtilis* genomic DNA using the primers: Ppan-EcoRI-up (5' "CCG GAA TTC GCT AAT GTG TTG GTA CAA GCC CG"; SEQ ID NO:2) and Ppan-BamHI-low (5' "CGC GGA TCC CAA TAA AGG TAT TCG GCG CAC CC"; SEQ ID NO:3).

Figure 2:
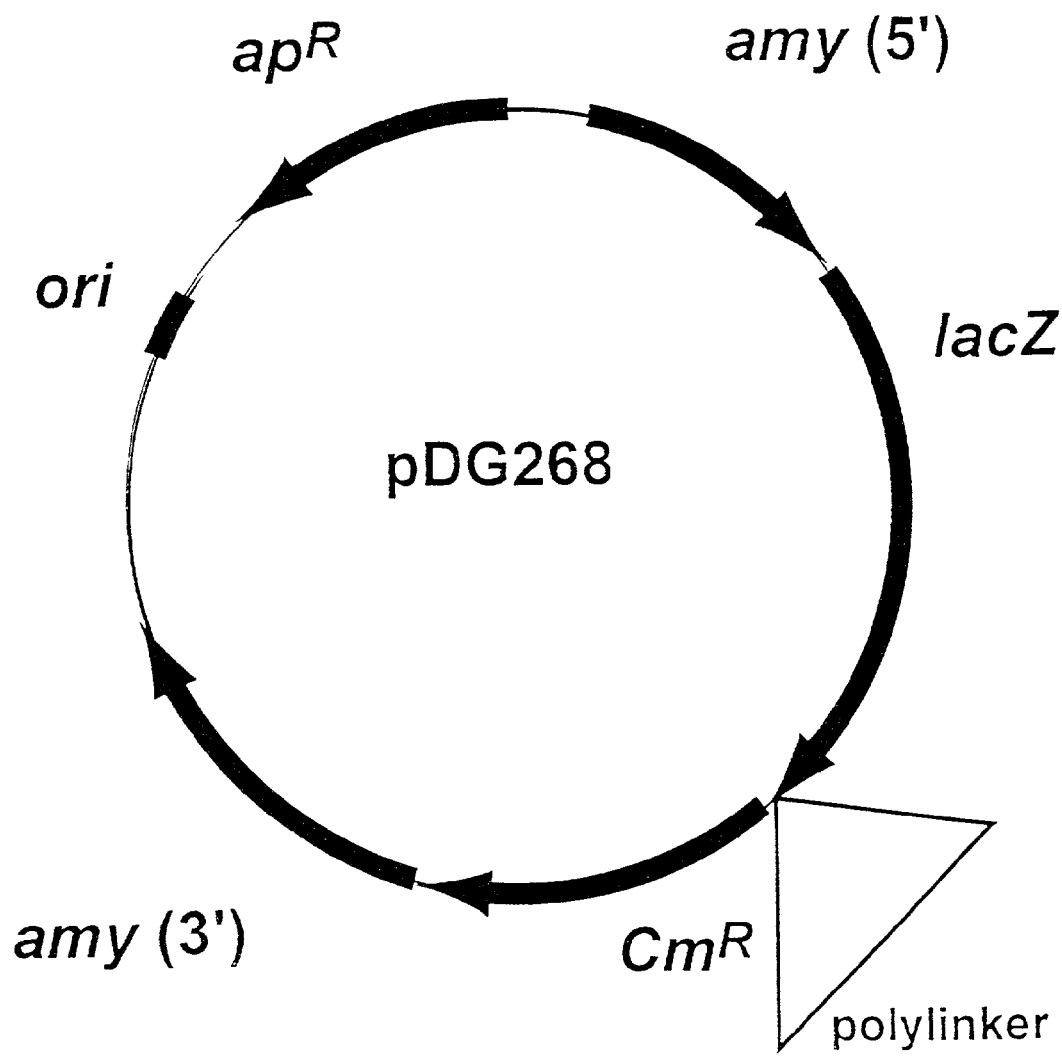
FIG. 2 is a map of the pDG268 vector.

The reporter strains used in these assays were constructed as follows. PCR products containing the promoters were digested with EcoRI and BamHI, and cloned into the multiple cloning site of pDG268, which also had been digested with EcoRI and BamHI. The plasmid pDG268 is a derivative of pGD364 (See, Cutting and Van der Horn, *Molecular Biological Methods for Bacillus*, eds. C. R. Harwood and S. M. Cutting, 1990, John Wiley and Sons, NY, N.Y. pp. 52–54). A schematic representation of pDG268 is set forth in FIG. 2. The plasmid pDG268 is able to replicate in *E. coli*, contains an ampicillin-resistance gene, and encodes a promoter-less lacZ coding sequence. The multiple cloning site (MCS) is positioned such that a promoter of interest can be directionally cloned to drive expression of the lacZ sequence. Adjacent to the MCS, and opposite the lacZ sequence, is a gene encoding chloramphenicol (Cm) resistance for *B. subtilis*. The entire Cm-MCS-lacZ region is flanked by the upstream and downstream section of the *B. subtilis* amyE gene (a "silent" locus in the *B. subtilis* chromosome). Thus, the promoter fusion of interest can be stably integrated by homologous recombination at the amyE site of the *B. subtilis* chromosome by transforming *B. subtilis* cells with the linearized plasmid, and selecting for resistance to chloramphenicol. The promoter fusions were placed at the amyE chromosomal location of the *B. subtilis* strain PY79, which is a wild-type *B. subtilis* strain that is devoid of prophages (Youngman et al., 1984, *Mol. Gen. Genet.* 195:424–433), resulting in strain PY79(amy:: PpanB::lacZ, cat).

Figure 3:
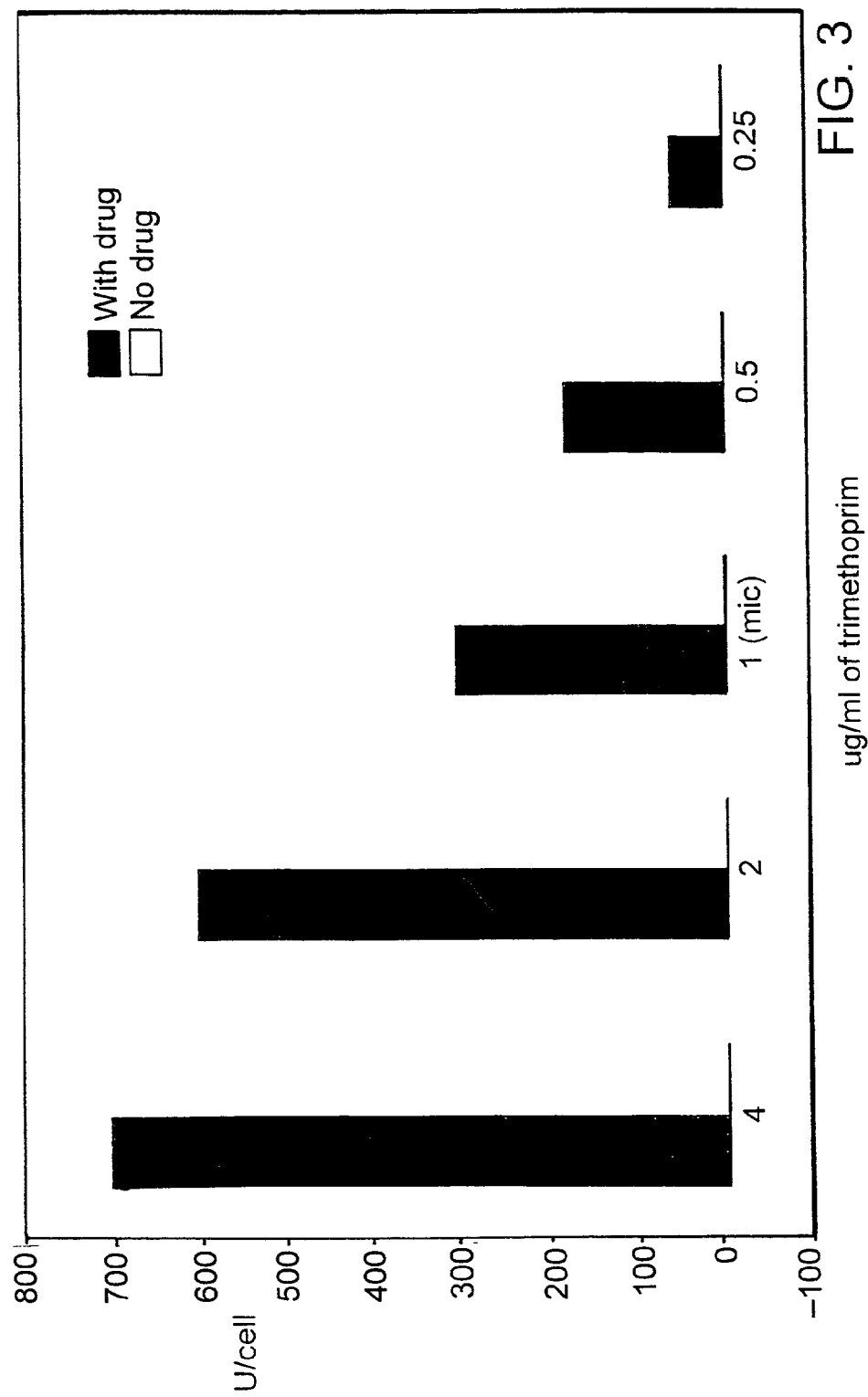
FIG. 3 is a histogram depicting the level of β-galactosidase induction of a plasmid containing the panB promoter operably linked to the lacZ gene after 5 hours of exposure to 4 μg/ml, 2 μg/ml, 1 μg/ml, 0.5 μg/ml, and 0.25 μg/ml of trimethoprim (with drug) in comparison to a mock treated control (no drug).
Figure 4:
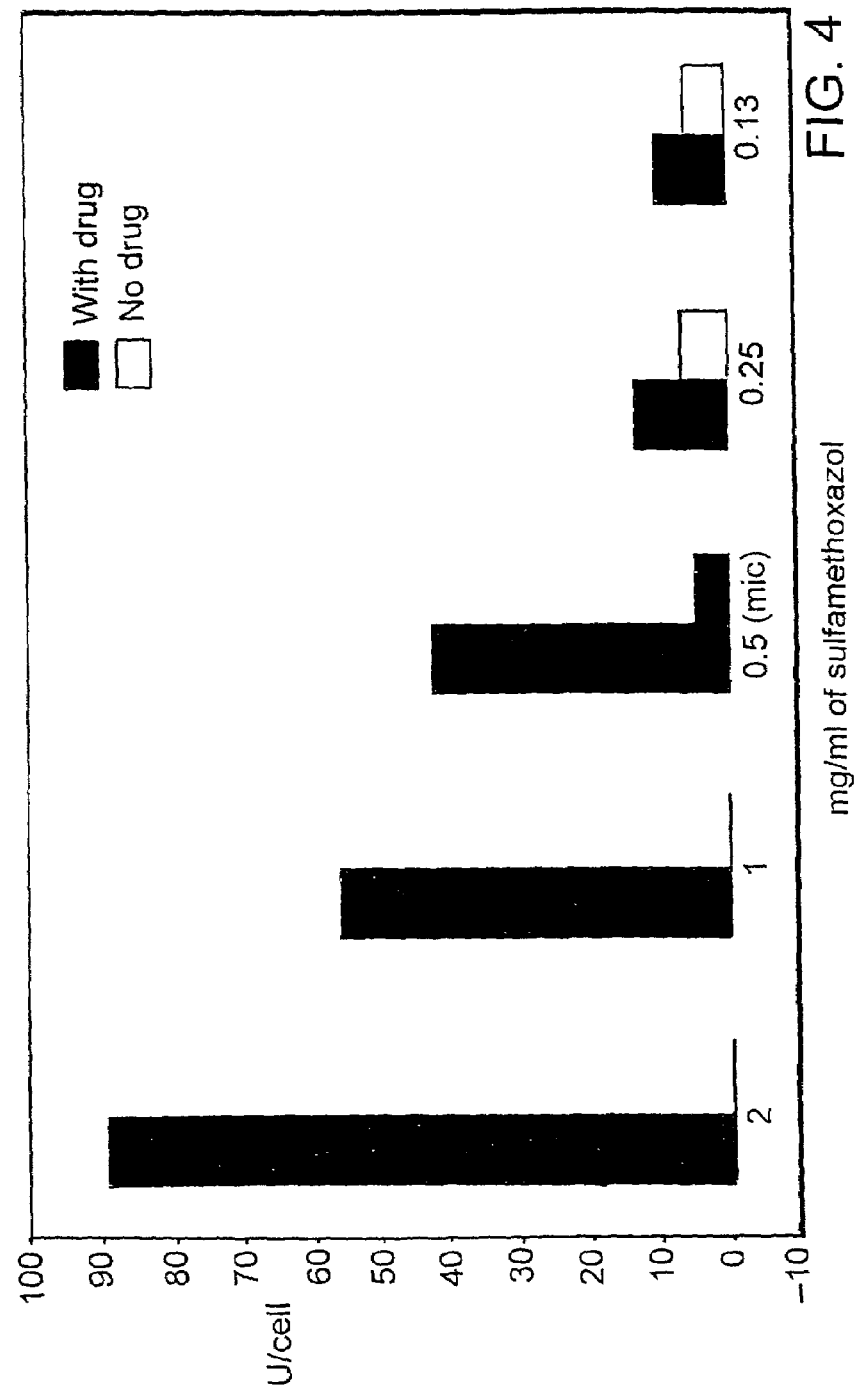
FIG. 4 is a histogram depicting the level of β-galactosidase induction of a plasmid containing the panB promoter operably linked to the lacZ gene after 5 hours of exposure to 2 mg/ml, 1 mg/ml, 0.5 mg/ml, 0.25 mg/ml, and 0.13 mg/ml of sulfamethoxazole (with drug) in comparison to a mock treated control (no drug).

The reporter strains were incubated, separately, with trimethoprim (FIG. 3) or sulfamethoxazole (FIG. 4) at various concentrations, as shown by the different bars of the histogram. The strain PY79(amy::PpanB::lacZ, cat) and an antibacterial agent were incubated in a 96-well microplate for 5 hours. β-galactosidase activity was detected using the Tropix Galacton Star™ chemiluminescent substrate (3-chloro-5-(4-methoxyspiro{1,2-dioxetane-3,2'-(4' chloro)-tricyclo-[3.3.1.1$^{3,7}$] decan}-4-yl)phenyl-B-D-galactopyranoside) and the detection method described below. The fold induction of promoter activity was calculated as the level of activity in the samples containing the antibacterial agent divided by the level of activity in the samples that lacked the agent.

The minimum inhibitory concentrations (MIC) for trimethoprim and sulfamethoxazole were determined for each of the reporter strains. To determine the MIC, a compound of interest (e.g., trimethoprim or sulfamethoxazole) was placed in a 96-well microtiter plate such that the concentration of the compound varies in various wells of the plate (e.g., by using a series of 2-fold dilutions of the compound). Approximately 5,000 cells from a logarithmically-growing culture (e.g., the *B. subtilis* strain PY79) in Luria broth were added to each well (e.g., in a volume of 50–80 μl). The plate then was incubated at 37° C. for approximately 18 hours. The $OD_{600}$ was then read to measure cell growth in each well of the plate. The lowest concentration of the compound that leads to complete killing of the culture (i.e., the concentration of compound for which the $OD_{600}$ nm is equal to a control well that contains only media and the test compound) is deemed the MIC for the particular compound and bacterial strain. The MICs for trimethoprim and sulfamethoxazole were 3 μg/ml and 500 μg/ml, respectively, in the reporter strain.

Example 2

Assay for Inhibitors of Tetrahydrofolate Biosynthesis

Having determined that antibacterial agents such as trimethoprim and sulfamethoxazole, increase the activity of the panB promoter, bacterial strains containing this promoter operably linked to a reporter gene (e.g., lacZ) can be used in a method for determining whether a test compound is an inhibitor of tetrahydrofolate biosynthesis. The following example of such a method describes use of the panB promoter in an initial assay. Comparable reagents, apparatuses, and methods can readily be substituted for those described herein.

Bacterial Strains: The bacterial strain PY79 (amy::Ppan-B::lacZ, cat), which contains the panB promoter operably linked to the coding sequence of a lacZ reporter gene, was used in the initial screen for inhibitors of tetrahydrofolate biosynthesis. To prepare a bacterial glycerol stock, the cell culture was mixed at a 1:1 ratio with sterile 50% glycerol, and 1.0 ml aliquots of the suspension were stored in cryovials at −80° C.

To prepare cells for use in the assay of test compounds, 5 μl of the glycerol stock is diluted in 80 ml of low salt LB medium (LB broth containing 5 g/L of NaCl). A 15 μl aliquot of this diluted glycerol stock is then added to 900 ml of low salt LB medium and grown to an $OD_{600}$ of 0.6 in a shaking incubator at 30° C. Generally, a culture having an $OD_{600}$ of 0.4 to 0.6 is suitable for use in the screening assays.

Screening Plates: In this example, chemical libraries containing test compounds at 10 mg/ml in DMSO are diluted to 100 μg/ml with 50 mM HEPES buffer (pH 7.4). The test compounds (e.g., 0.1 μg or 0.05 μg) are dispensed into each well of a microplate (e.g., a 96- or 384-well microplate). The dispensed compounds are dried onto the plates (e.g., by leaving the plates in a fume hood overnight), and the plates are stored in the freezer and then brought to room temperature before being used in the screening assay.

A 50 μl sample of the bacteria is added to each well of the microplate. Trimethoprim is used as a control in wells of the microplate that lack a test compound. A stock solution of trimethoprim is prepared to a concentration of 10 mg/ml in DMSO and stored at −20° C. A working solution of trimethoprim is prepared by diluting the trimethoprim stock solution to 10 μg/ml with 50 mM HEPES (pH 7.4). A 5 μl aliquot of the 10 μg/ml of trimethoprim working solution is added to the plate to provide a control. The bacteria and test compounds (or trimethoprim control) are then incubated at 30° C. for approximately 5 hours. If desired, the length and/or temperature of incubation can be increased or decreased. After incubating the cells and test compounds, the plates can be stored at −80° C. if they are not going to be analyzed immediately. Before analysis, the plates should be returned to room temperature, e.g., by leaving the plates in a single layer for one hour at room temperature.

Assay for Induction of Promoter Activity: To assay for an increase in the activity of the panB promoter, an increase in expression of the lacZ reporter gene expression (or expression of an alternative reporter gene) is measured. A 50 μl aliquot of 2× substrate buffer is added to each well of the plate. To produce a 10 ml sample of 2× substrate buffer, the following components are mixed and kept at room temperature: 0.4 ml of Galacton-Star™ substrate (3-chloro-5-(4-methoxyspiro{1,2-dioxetane-3,2'-(4'chloro)-tricyclo-[3.3.1.1$^{3,7}$] decan}-4-yl)phenyl-B-D-galactopyranoside; Tropix, Inc., Cat.# GS100); 2.0 ml of Sapphire II™ luminescence signal enhancer (Tropix, Inc., Cat.#LAX250); and 7.6 ml of lysis buffer (0.026% Na Deoxycholic acid, 0.053% CTAB, 265 mM NaCl, 395 mM HEPES, pH 7.5). The 2× substrate buffer is stable for approximately 2 hours. The plates are incubated at room temperature for 120 minutes before measuring β-galactosidase activity.

A chemiluminescent signal is produced by reaction of β-galactosidase with the Galacton-Star™ substrate (3-chloro-5-(4-methoxyspiro{1,2-dioxetane-3,2'-(4'chloro)-tricyclo-[3.3.1.1$^{3,7}$] decan}-4-yl)phenyl-B-D-galactopyranoside). Chemiluminescence is measured using a TopCount™ microplate reader set as follows: data mode=seconds per count; count time=0.1 minute; count delay=0.10 minute; background subtract=none; half-life correction=no; sample screening=no; and quench indicator=tSIS. Generally, chemiluminescence should be measured before significant signal decay occurs. The read window for the substrate, during which time the plates should be analyzed, is approximately 120 minutes to 180 minutes after initiating the reaction.

The mean and standard deviation of the results obtained for the reactions on a particular plate are measured (excepting the trimethoprim control wells). A chemiluminescent signal that is at least 3 times the standard deviation, plus the mean, indicates that the test compound is a lead or candidate compound, i.e., a compound that increases the activity of the promoter and is a tetrahydrofolate biosynthesis inhibitor. The trimethoprim controls described above should produce a chemiluminescent signal that is at least equal to 4 times the mean. The general quality of the analysis of the plate can be determined using Spotfire Pro version 4.0 data analysis software (Spotfire, Inc.; Cambridge, Mass.) by assessing parameters such as the overall hit rate, the random nature of the position of hits, and signal strength consistency over all plates and analyses. Compounds that inhibit tetrahydrofolate biosynthesis may or may not be bacteriocidal or bacteriostatic. Nevertheless, such compounds can be used in the development of antibacterial drugs through the use of standard medicinal chemistry techniques. Thus, the invention includes methods for preparing an antibacterial agent by: screening multiple test compounds as described herein to identify candidate compounds that upregulate promoter activity and therefore are tetrahydrofolate biosynthesis inhibitors; isolating one or more lead compounds from the candidate compounds; determining whether the compound inhibits the growth of a bacterium, in which case the compound can be formulated as an antibacterial agent; and, optionally, derivatizing the lead compound(s) through medicinal chemistry to produce a derivative(s) that inhibits the growth of a bacterium; and formulating the derivative as an antibacterial agent. Optionally, the compound can be characterized in a biochemical assay to determine which step it inhibits in the tetrahydrofolate biosynthesis pathway and/or confirm that the protein is a tetrahydrofolate biosynthesis inhibitor.

Example 3

Confirmatory Metabolite Uptake Assay

Test compounds that cause an induction of promoter activity of at least 3 times the standard deviation, plus the mean, can be further tested (e.g., at 10 μg/ml and 50 μg/ml) in an optional, "confirmatory" assay. In one implementation, a cell-based metabolite uptake assay is used as the "confirmatory" assay. Cells are grown in Luria Broth supplemented with 100 μg/ml thymidine. Carboxyl $^{14}$C labeled PABA (60 mCi/mmol) is stored in ethanol at a concentration of $5 \cdot 10^6$ cpm/ml at 4° C. After approximately 16 hours of growth, cells are diluted 100 fold and $^{14}$C labeled PABA is added to the media at about 6700 cpm/ml. Test compounds are also added to the media of test cultures. Additional cultures are prepared with no additive or with trimethoprim or sulfamethoxazole added as controls. The cultures are grown with shaking for 20 to 24 hours at 30° C. Subsequently, cells are filtered through a Sartorius 0.22 μm cellulose nitrate filter and washed with media. Samples are processed in parallel on a manifold. The filters are then placed in scintillation fluid and counted using a scintillation counter. Cell densities can be determined by measuring the optical density of the remainder of the culture. The amount of PABA incorporated can be determined by dividing the scintillation counts detected by the optical density. The mean and standard deviation are determined using the values obtained with multiple wells (minus the values of trimethoprim controls). An example of the effect of trimethoprim and sulfathiazole on PABA uptake is illustrated in FIG. 1 (Herrington. Ibid.).

Example 4

Biochemical Assay of Inhibition of Tetrahydrofolate Biosynthesis:

If desired, test compounds identified as candidate antibacterial agents in the above-described assays can be further tested for their ability to inhibit tetrahydrofolate biosynthesis in a biochemical assay. For example, compounds identified in the above-described assay can be further tested for their ability to inhibit the enzymes encoded by tetrahydrofolate biosynthesis genes, such as mtrA, folA, folK, sul, pabA, pabB, pabC, folC, and dfrA. The reactions catalyzed by each of these gene products are set forth above in Table 1, and methods for assaying these reactions are known in the art.

In one implementation, candidate compounds can be assayed for their ability to inhibit *B. subtilis* dihydrofolate reductase as described in Myoda et al. (1984) Gene 29:135–143. *B. subtilis* cells resuspended in 50 mM Tris.HCl, pH 7.4 10 mM 2-mercaptoethanol, and incubated with 200 μg/ml lysozyme and 10 μg/ml deoxyribonuclease I for 30 minutes at 37° C. Cells are then sonicated at 4° C. with three 90 second bursts interspersed with 30 second cooling intervals. Cell debris is pelleted by centrifugation at 30 000 g for 20 minutes. Protein concentration is determined by the Bradford method using a kit (Bio-Rad). A 1 ml reaction mixture is supplemented with 50 nmol NADPH, 10 μmol 2-mercaptoethanol, and 25 mM potassium phosphate pH 7.0. The reaction is carried out at 30° C. and followed with a spectrophotometer at 340 nm. The candidate compound is added at a range of concentrations to one set of reaction mixtures while another set of reaction mixtures lacking the candidate compound is tracked in parallel as a control. The reaction can be initiated by the addition of 60 nmol dihydrofolic acid (DHF). Dihydrofolate reductase specific activity can expressed as nmol of DHF reduced/min/mg of protein using an extinction coefficient of 11 650.

OTHER EMBODIMENTS

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for determining whether a test compound is an inhibitor of bacterial tetrahydrofolate biosynthesis, the method comprising:
   (i) contacting a bacterial cell with a test compound, wherein the bacterial cell contains a panB promoter, the activity of which is increased in the presence of a compound that inhibits tetrahydrofolate biosynthesis; and
   (ii) measuring activity of the panB promoter, wherein an increase in activity, relative to the level of activity of the promoter in the absence of the test compound, indicates that the test compound is an inhibitor of bacterial tetrahydrofolate biosynthesis.

2. A method of claim 1, wherein the panB promoter comprises a nucleic acid sequence as set forth in SEQ ID NO:1 or a fragment thereof.

3. A method of claim 1, wherein the activity of the promoter is measured by an antibody specific for a polypeptide selected from the group consisting of: aspartate 1-decarboxylase, pantothenate synthase, and ketopantoate hydroxymethyltransferase.

4. A method of claim 1, wherein the activity of the promoter is measured by an assay for the activity of an enzyme selected from the group consisting of: aspartate 1-decarboxylase, pantothenate synthase, and ketopantoate hydroxymethyltransferase.

5. A method of claim 1, wherein the activity of the promoter is measured by detecting the RNA species transcribed from the gene regulated by the promoter.

6. A method of claim 1, wherein the cell contains the promoter operably linked to a reporter gene.

7. A method of claim 6, wherein the reporter gene is selected from the group consisting of lacZ, cat, gus, a luciferase gene, and a green fluorescent protein gene.

8. A method for determining whether a test compound is an inhibitor of bacterial tetrahydrofolate biosynthesis, the method comprising:
   (i) contacting a bacterial cell with a test compound, wherein the bacterial cell contains
      (a) a panB promoter, the activity of which is increased in the presence of a compound that inhibits tetrahydrofolate biosynthesis, operably linked to
      (b) a reporter gene; and
   (ii) measuring activity of the panB promoter, wherein an increase in activity, relative to the level of activity of the promoter in the absence of the test compound, indicates that the test compound is an inhibitor of bacterial tetrahydrofolate biosynthesis.

9. A method of claim 8, wherein the reporter gene is selected from the group consisting of lacZ cat, gus, a luciferase gene, and a green fluorescent protein gene.

10. A method of claim 8, wherein measuring an increase in activity of the promoter comprises measuring binding of antibodies to a product of the reporter gene.

11. A method of claim 8, wherein the panB promoter comprises a nucleic acid sequence as set forth in SEQ ID NO:1 or a fragment thereof.

12. A method for determining whether a test compound is an antibacterial agent, the method comprising:
   (i) contacting a bacterial cell with a test compound, wherein the bacterial cell contains
      (a) a panB promoter, the activity of which is increased in the presence of a compound that inhibits tetrahydrofolate biosynthesis, operably linked to
      (b) a reporter gene;
   (ii) measuring activity of the panB promoter, wherein an increase in activity, relative to the level of activity of the promoter in the absence of the test compound, indicates that the test compound is an inhibitor of bacterial tetrahydrofolate biosynthesis; and
   (iii) determining whether the inhibitor of tetrahydrofolate biosynthesis inhibits the growth of a bacterium, wherein a compound that inhibits the growth of a bacterium is an antibacterial agent.

13. A method of claim 12, further comprising assaying the test compound for its ability to inhibit tetrahydrofolate biosynthesis.

14. A method of claim 13, wherein inhibition of tetrahydrofolate biosynthesis is detected as inhibition of para-aminobenzoic acid (PABA) uptake into cells.

15. A method of claim 13, wherein inhibition is measured in a biochemical assay with a cell extract for an enzyme activity which is required for tetrahydrofolate biosynthesis.

16. A method of claim 15 wherein the enzyme activity assayed is selected from the group consisting of: GTP cyclohydrase, 7,8 dihydroneopterin aldolase, 6-hydroxymethyl-7,8-dihydropterin pyrophosphokinase, dihydropteroate synthase, aminodeoxychorismate synthase, aminodeoxychorismate lyase, dihydrofolate:foly-polyglutamate synthase, and dihydrofolate reductase.

17. A method of preparing an inhibitor of bacterial tetrahydrofolate biosynthesis, the method comprising:
   screening multiple test compounds by the method of claim 8;
   identifying candidate compounds that increase promoter activity;
   identifying, and selecting from the candidate compounds a lead compound that inhibits bacterial tetrahydrofolate biosynthesis; and
   formulating the selected lead compound as an inhibitor of bacterial tetrahydrofolate biosynthesis.

18. A method of preparing an antibacterial agent, the method comprising:
   screening multiple test compounds by the method of claim 12;
   identifying candidate compounds that upregulate promoter activity;
   identifying and selecting from the candidate compounds a lead compound that inhibits growth of a bacterium; and
   formulating the selected lead compound as an antibacterial agent.

19. The method of claim 1, wherein the panB promoter is a *Bacillus subtilis* panB promoter.

20. The method of claim 8, wherein the panB promoter is a *Bacillus subtilis* panB promoter.

21. The method of claim 12, wherein the panB promoter is a *Bacillus subtilis* panB promoter.

22. The method of claim 17, wherein the panB promoter is a *Bacillus subtilis* panB promoter.

23. The method of claim 18, wherein the panB promoter is a *Bacillus subtilis* panB promoter.

* * * * *